United States Patent [19]

Dobbs

[11] Patent Number: 5,380,520
[45] Date of Patent: Jan. 10, 1995

[54] COSMETIC FILM FORMING COMPOSITIONS WHICH ARE FREEZE-THAW STABLE

[75] Inventor: Suzanne W. Dobbs, Kingsport, Tenn.

[73] Assignee: Eastman Chemical Company, Kingsport, Tenn.

[21] Appl. No.: 114,854

[22] Filed: Sep. 2, 1993

[51] Int. Cl.$^6$ .................. A61K 7/04; A61K 7/043
[52] U.S. Cl. ..................... 424/61; 424/401; 524/765; 524/783; 524/796; 524/817; 524/185; 524/714; 524/724; 524/770; 528/272
[58] Field of Search ............... 424/401, 61; 524/765, 524/783, 714, 785, 796, 817, 770, 724; 528/272

[56] References Cited

U.S. PATENT DOCUMENTS

| | | | |
|---|---|---|---|
| 4,158,053 | 6/1979 | Greene et al. | 424/61 |
| 4,254,104 | 3/1981 | Suzuki | 424/47 |
| 4,474,912 | 10/1984 | Ozermal et al. | 524/491 |
| 4,939,233 | 7/1990 | Jenkins et al. | 528/272 |
| 4,946,932 | 8/1990 | Jenkins | 528/272 |
| 5,266,303 | 11/1993 | Myers et al. | 424/71 |
| 5,266,322 | 11/1993 | Myers et al. | 424/78.08 |

Primary Examiner—D. Gabrielle Phelan
Assistant Examiner—Peter F. Kulkosky
Attorney, Agent, or Firm—John D. Thallemer

[57] ABSTRACT

This invention relates to a cosmetic film forming composition which is freeze-thaw stable and is especially useful as a nail coating composition which upon drying forms a film which will adhere to keratin of a nail. More particularly, the present invention relates to cosmetic film forming compositions which consist of aqueous emulsion (A) which comprises a sulfopolyester and a copolymer of vinyl acetate and dialkyl maleate or fumarate; aqueous emulsion (B) which comprises an aqueous emulsion polymer of acetoacetoxyethyl alkylacrylate or the polymerization reaction product of acetoacetoxyethyl alkylacrylate with a vinylfunctional monomer; and (C) a freeze-thaw agent. The freeze-thaw agent imparts improved freeze-thaw properties to the composition without being detrimental to desirable properties such as fast drying time and good adhesive properties.

26 Claims, No Drawings

COSMETIC FILM FORMING COMPOSITIONS WHICH ARE FREEZE-THAW STABLE

FIELD OF THE INVENTION

This invention relates to a cosmetic film forming composition which is freeze-thaw stable and is especially useful as a nail coating composition which upon drying forms a film which will adhere to keratin of a nail. More particularly, the present invention relates to cosmetic film forming compositions which consist of aqueous emulsion (A) which comprises a sulfopolyester and a copolymer of vinyl acetate and dialkyl maleate or fumarate; aqueous emulsion (B) which comprises an aqueous emulsion polymer of acetoacetoxyethyl alkylacrylate or the polymerization reaction product of acetoacetoxyethyl alkylacrylate with a vinylfunctional monomer; and (C) a freeze-thaw agent. The freeze-thaw agent imparts improved freeze-thaw properties to the composition without being detrimental to desirable properties such as fast drying time and good adhesive properties.

BACKGROUND OF THE INVENTION

Many types of cosmetic film forming compositions including nail coating formulations are available. The majority of such nail coatings are lacquers which consist of a nitrocellulose, aryl sulfonamide formaldehyde resin, plasticizer and organic solvent mixture together with a small proportion of colorant and other ingredients. These nail lacquers have the disadvantages of poor moisture vapor transmission, discoloration of the nail, and require a long drying time. In addition, the nail lacquers contain volatile organic solvents which cause safety, toxicological and environmental concerns.

Film forming compositions have been disclosed in U.S. Pat. Nos. 4,939,233, 4,946,932 and 4,158,053. U.S. Pat. No. 4,939,233 discloses film forming compositions that contain a polyester having repeat units from at least one difunctional sulfomonomer containing at least one metal sulfonate group attached to an aromatic nucleus wherein the functional groups are carboxyl or hydroxyl, and an addition polymer having a majority of repeat units from vinyl acetate, wherein the later polymer is formed from monomers polymerized in an aqueous dispersion of said polyesters. The use of such compositions in nail polishes, produce films that exhibit poor adhesion, poor durability and poor water resistance.

U.S. Pat. No. 4,946,932 discloses film forming compositions that contain an aqueous dispersion of a sulfonate group-containing polyester or polyesteramide and a polymer comprising repeat units from one or more $\alpha,\beta$-unsaturated monomers. The use of such compositions in nail polishes, produce films that exhibit poor adhesion, poor durability and poor water resistance.

U.S. Pat. No. 4,158,053 discloses aqueous nail coating formulations which are prepared by an aqueous emulsion polymerization of two or more monomers selected from alkyl acrylates, alkyl methacrylates and styrene compounds. The use of such formulations on nails, produce slow drying films that exhibit poor adhesion and poor durability.

U.S. application Ser. No. 07/890,419 describes cosmetic film forming compositions which consist of an aqueous emulsion which comprises a sulfopolyester and a copolymer of vinyl acetate and dialkyl maleate, and an aqueous emulsion which comprises an aqueous emulsion of acetoacetoxyethyl alkylacrylate or the reaction product of acetoacetoxyethyl alkylacrylate with a vinylfunctional monomer. The cosmetic film forming compositions of U.S. application Ser. No. 07/890,419 are fast drying, have good adhesive properties and are environmentally compatible. However, when such compositions are exposed to one or more freeze-thaw cycles involving temperatures below 0° C. for several hours to produce solidification of the composition and then allowed to thaw, undesirable solid material remains which impedes storage of the cosmetic compositions.

Thus, it would be highly desirable if a new cosmetic film forming composition could be developed having good freeze-thaw stability while maintaining water resistance, durability, vapor transmission, hold out, less odor, fast drying times and high gloss without the presence of volatile organic compounds.

SUMMARY OF THE INVENTION

Accordingly, it is one object of the present invention to provide a freeze-thaw stable cosmetic film forming composition.

Another object of this invention is to provide a cosmetic film forming composition which is freeze-thaw stable and has little or no volatile organic content.

These and other objects are accomplished herein by a freeze-thaw stable cosmetic film forming composition comprising:

(A) 27.5 to 85 weight percent of an aqueous emulsion comprising
  (1) a sulfopolyester consisting essentially of repeat units from
    (a) a dicarboxylic acid selected from the group consisting of aromatic dicarboxylic acids, saturated aliphatic dicarboxylic acids, cycloaliphatic dicarboxylic acids, and combinations thereof;
    (b) a diol; and
    (c) a difunctional sulfomonomer containing at least one sulfonate group attached to an aromatic nucleus wherein the functional groups are hydroxy, carboxy or amino, provided the difunctional sulfomonomer is present in an amount from 4 to 25 mole percent based on 100 mole percent dicarboxylic acid and 100 mole percent diol; and
  (2) a copolymer having repeat units from 50 to 90 weight percent vinyl acetate and 10 to 50 weight percent of a dialkyl maleate or fumarate having the formula

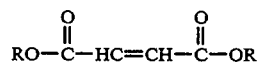

which is polymerized in an aqueous dispersion of the sulfopolyester;

(B) 12.5 to 70 weight percent of an aqueous emulsion of an addition polymer derived by emulsion polymerization of acetoacetoxyethyl alkylacrylate having the formula:

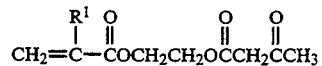

or a polymerization reaction product of acetoacetoxyethyl alkylacrylate with a vinyl-functional monomer selected from the group consisting of

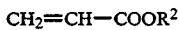

(I)

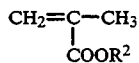

(II)

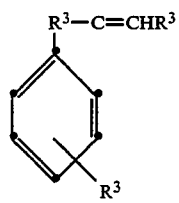

and mixtures thereof;
wherein: R is a monovalent alkyl radical having 1 to 12 carbon atoms, $R^1$ is a monovalent alkyl radical having 1 to 4 carbon atoms, $R^2$ is selected from the group consisting of an alkyl radical having 1 to 20 carbon atoms, a substituted alkyl radical having 1 to 20 carbon atoms, phenyl, substituted phenyl, cycloalkyl, furfuryl, and tetrahydrofurfural, and $R^3$ is independently selected from the group consisting of hydrogen and an alkyl radical having 1 to 4 carbon atoms; and (C) 2.5 to 10 weight percent of a freeze-thaw agent selected from the group consisting of glycerine, polyethylene glycol 200, polyethylene glycol 300, propylene glycol, dipropylene glycol, sorbitol, and combination thereof; provided that glycerine, polyethylene glycol 200, polyethylene glycol 300 or combinations thereof constitute at least 1.7 weight percent of the total combined weight of components (A), (B) and (C); and further provided that the total solids in the film forming composition is from 30 to 65 weight percent.

DESCRIPTION OF THE INVENTION

Aqueous emulsion (A) contains a sulfopolyester and a copolymer. The sulfopolyester, component (1), contains repeat units from a dicarboxylic acid, a diol and a difunctional sulfomonomer. Dicarboxylic acids useful in the present invention include aromatic dicarboxylic acids preferably having 8 to 14 carbon atoms, saturated aliphatic dicarboxylic acids preferably having 4 to 12 carbon atoms, and cycloaliphatic dicarboxylic acids preferably having 8 to 12 carbon atoms, Specific examples of dicarboxylic acids are: terephthalic acid, phthalic acid, isophthalic acid, naphthalene-2,6-dicarboxylic acid, cyclohexanedicarboxylic acid, cyclohexanediacetic acid, diphenyl-4,4'-dicarboxylic acid, succinic acid, glutaric acid, adipic acid, azelaic acid, sebacic acid, and the like. The polyester may be prepared from two or more of the above dicarboxylic acids.

It should be understood that use of the corresponding acid anhydrides, esters, and acid chlorides of these acids is included in the term "dicarboxylic acid".

The diol component of the polyester includes cycloaliphatic diols preferably having 6 to 20 carbon atoms or aliphatic diols preferably having 2 to 20 carbon atoms. Examples of such diols are: ethylene glycol, diethylene glycol, triethylene glycol, 1,4-cyclohexanedimethanol, propane-1,3-diol, butane-1,4-diol, pentane-1,5-diol, hexane-1,6-diol, 3-methylpentanediol-(2,4), 2-methylpentanediol-(1-(1,4), 2,2,4-trimethylpentane-diol-(1,3), 2-ethylhexanediol-(1,3), 2,2-diethylpropane-diol-(1,3), hexanediol-(1,3), 1,4-di-(hydroxyethoxy)-benzene, 2,2-bis-(4-hydroxycyclohexyl)-propane, 2,4-dihydroxy-1,1,3,3-tetramethyl-cyclobutane, 2,2-bis-(3-hydroxyethoxyphenyl)-propane, and 2,2-bis(4-hydroxypropoxyphenyl)-propane. The polyester may be prepared from two or more of the above diols.

The difunctional sulfomonomer component of the polyester may be a dicarboxylic acid or an ester thereof containing a sulfonate group (—SO₃—), a diol containing a sulfonate group, or a hydroxy acid containing a sulfonate group. The cation of the sulfonate salt may be Na+, Li+, K+, NH₄+, or substituted ammonium. The term "substituted ammonium" refers to ammonium substituted with an alkyl or hydroxy alkyl radical having 1 to 4 carbon atoms. The difunctional sulfomonomer contains at least one sulfonate group attached to an aromatic nucleus wherein the functional groups are hydroxy, carboxy or amino. Advantageous difunctional sulfomonomer components are those wherein the sulfonate salt group is attached to an aromatic acid nucleus such as benzene, naphthalene, diphenyl, oxydiphenyl, sulfonyldiphenyl or methylenediphenyl nucleus. Preferred results are obtained through the use of sulfophthalic acid, sulfoterephthalic acid, sulfoisophthalic acid, 4-sulfonaphthalene-2,7-dicarboxylic acid, and their esters. The sulfomonomers is present in an amount from 4 to 25 mole percent based on 100 mole percent dicarboxylic acid and 100 mole percent diol.

Component (2) is a copolymer having repeat units from 50 to 90 weight percent vinyl acetate and 10 to 50 weight percent of a dialkyl maleate or fumarate. The dialkyl maleate or fumarate has the general formula:

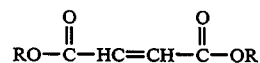

R in the above formula is a monovalent alkyl radical having 1 to 12 carbon atoms. The vinyl acetate and dialkyl maleate are polymerized in an aqueous dispersion containing the sulfopolyester (1), to form a copolymer (2). Preferably, the dialkyl maleate is dibutyl maleate. It is important to note that ethylene may be substituted for the dialkyl maleate or fumarate under certain processing conditions to achieve a satisfactory cosmetic film forming composition.

It is preferred that the copolymer (2) be comprised of units derived from vinyl acetate present at levels at about 80 weight percent and units derived from a dialkyl maleate present at levels of about 20 weight percent. It is also preferred that aqueous emulsion (A) consist of from about 5 to about 20 weight percent of sulfopolyester (1) and from about 80 to about 95 weight percent of copolymer (2).

Component (B) of the present invention is an aqueous emulsion containing an addition polymer derived by emulsion polymerization of acetoacetoxyethyl alkylacrylate having the formula:

$R^1$ in the above formula is a monovalent alkyl radical having 1 to 4 carbon atoms. Preferably, the acetoacetoxyethyl alkylacrylate is acetoacetoxyethyl methacrylate. Component (B) may also be a polymerization reaction product of acetoacetoxyethyl alkylacrylate with a vinylfunctional monomer of formulae I–III:

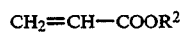  (I)

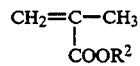  (II)

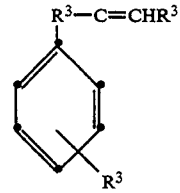

In formulae I–III, $R^2$ is selected from an alkyl radical having 1 to 20 carbon atoms, a substituted alkyl radical having 1 to 20 carbon atoms, phenyl, substituted phenyl, cycloalkyl, furfuryl, and tetrahydrofurfural. $R^3$ is independently selected from hydrogen and an alkyl radical having 1 to 4 carbon atoms. The term "substituted alkyl" refers to an alkyl radical substituted with phenyl, substituted phenyl, cycloalkyl, hydroxy, epoxy, $C_1$ to $C_4$ alkoxy, or $-N(R^4)R^5$ group. $R^4$ and $R^5$ are independently selected from hydrogen, $C_1$ to $C_8$ alkyl, and $C_1$ to $C_8$ hydroxy alkyl. Examples of substituted alkyl groups are 2-hydroxyethyl, 2-ethoxyethyl, benzyl, 2-phenylethyl, 2,3-epoxy-1-propyl, cyclohexylmethyl, 2-cyclohexylethyl, 2,3-dihydroxypropyl, 2-dimethylaminoethyl, 3-diethylaminopropyl, and 2-[(N,N-di-2-hydroxyethyl)amino]ethyl.

The term "substituted phenyl" refers to a phenyl radical substituted with one or more groups selected from $C_1$ to $C_4$ alkyl, $C_1$ to $C_4$ alkoxy, and halogen. Examples of substituted phenyl groups are 4-methylphenyl, 3,4-dimethylphenyl, 3-methylphenyl, 2-chlorophenyl, 4-chlorophenyl, 2,5-dichlorophenyl, 4-ethoxyphenyl, 4-n-butylphenyl, 3-isopropoxyphenyl, 4-t-butyloxyphenyl, 2-ethoxy-5-methylphenyl and 2,5-diethoxyphenyl. The term "cycloalkyl" refers to a $C_3$ to $C_8$ cycloaliphatic monovalent radical such as cyclopentyl and cyclohexyl.

Mixtures of such vinyl-functional monomers may also be reacted with acetoacetoxyethyl methacrylate and used as aqueous emulsion (B). Aqueous emulsion (B) is present in an amount of from 12.5 to 70 weight percent, preferably 12.5 to 25 weight percent based on the total weight of components (A), (B) and (C).

Examples of suitable acrylate esters, formula I, are methyl acrylate, ethyl acrylate, butyl acrylate, benzyl acrylate, furfuryl acrylate, tetrahydrofurfuryl acrylate, methoxyethyl acrylate, ethoxyethyl acrylate, 2-ethylhexyl acrylate, cyclopentyl acrylate, cyclohexyl acrylate, 2,3-epoxy-1-propyl acrylate, 2-dimethylaminoethyl acrylate, and lauryl acrylate.

Examples of methacrylate esters, formula II, are methyl methacrylate, ethyl methacrylate, propyl methacrylate, butyl methacrylate, phenyl methacrylate, benzyl methacrylate, propyleneglycol monomethacrylate, stearyl methacrylate, tetrahydrofurfuryl methacrylate, furfuryl methacrylate, 2-diethylaminoethyl methacrylate and hydroxyethyl methacrylate.

Examples of suitable aromatic vinyl-functional monomers, formula III, are styrene, 4-vinyltoluene, 2-vinyltoluene, a-methylstyrene, 4-isopropylstyrene, and diisopropenyl benzene.

In addition to the above three classes of vinyl-functional monomers, formulas I, II and III, additional optional vinyl-functional monomers may be reacted with acetoacetoxyethyl alkylacrylate; however, the total amount of any of the optional vinyl-functional monomers should not exceed 10 percent by weight of the vinyl-functional monomers of formulae I–III, and should preferably be less than 5 percent by weight. The specific nature of the optional vinyl-functional monomer is not critical so long as the amount of any optional vinyl-functional monomer does not deleteriously effect the film forming properties of the formulations.

Components (A) and (B) of the present invention are prepared as aqueous emulsion polymers. In the case of aqueous emulsion (A), the vinyl acetate and dialkyl maleate or fumarate are added to an aqueous dispersion of the water-dispersible sulfopolyester and polymerized by free radical initiation in conventional emulsion or suspension polymerization processes. The polymerization can be initiated by a water-soluble free radical initiator known in the art such as sodium persulfate or by an oil-soluble initiator such as benzoyl peroxide. Other useful initiators include non-redox initiators and redox initiators. Examples of non-redox initiators are persulfate salts, hydrogen peroxide and organic peroxides. Examples of redox initiators are sodium persulfate, sodium bisulfite, sodium metabisulfite, sodium hydrosulfite, sodium thiosulfate, and sodium formaldehyde sulfoxylate. Redox initiators require an activator, such as ferrous sulfate heptahydrate, and ferrous ammonium sulfate. Preferred initiators are persulfate salts, sodium formaldehyde sulfoxylate, and ferrous sulfate heptahydrate.

The sulfopolyesters which are used in the present invention typically become very viscous at concentrations above 30 percent solids. Thus, the reaction typically is begun with a polyester dispersion that is about 30 percent total solids or less. However, the water-dispersible polyester dispersions which are prepared by the process of the present invention can be prepared at final total solids levels up to about 60 percent. The increase in solids level is achieved during polymerization by controlling the amount of water, if any, which is added along with the vinyl acetate and dialkyl maleate. By decreasing the amount of water added during the polymerization, increasing total solids contents up to about 60 percent is possible.

In a preferred embodiment, the sulfopolyester is prepared by melt polymerization, and an aqueous dispersion containing about 5–35 weight percent, preferably from about 10 percent to 30 percent total solids, is prepared from the sulfopolyester directly. A mixture of the vinyl acetate, dialkyl maleate and the polymerization initiators are then added to the aqueous dispersion of the sulfopolyester and polymerization initiated to produce an aqueous dispersion. The aqueous dispersion so produced can be prepared with total solids contents from about 10 percent to about 65 percent.

In the case of aqueous emulsion (B), the acetoacetoxyethyl methacrylate alone or in combination with a vinyl-functional monomer of Formulae I–III, is combined with water, initiator and surfactant, and polymerized by free radical initiation in conventional emulsion or suspension polymerization processes. The polymerization can be initiated by a water-soluble free radical initiator know in the art such as sodium persulfate or by an oil-soluble initiator such as benzoyl peroxide. Other useful initiators include non-redox initiators, such as persulfate salts, hydrogen peroxide, and organic peroxides; redox initiator, such as sodium persulfate, sodium bisulfite, sodium metabisulfite, sodium hydrosulfite, sodium thiosulfate, and sodium formaldehyde sulfoxylate. Redox initiators require an activator, such as ferrous sulfate heptahydrate, and ferrous ammonium sulfate. The preferred initiators are persulfate salts, sodium formaldehyde sulfoxylate, and ferrous sulfate heptahydrate.

More than one surfactant may be used, and a combination of anionic and non-anionic surfactants are possible. Cationic surfactants are rarely used. The anionic and non-anionic surfactants are preferred. Examples of suitable non-ionic surfactants are alcohol-ethylene oxide condensates, fatty acid-ethylene oxide condensates, phenol-ethylene oxide condensates, modified alkyl resins, and sorbitol-fatty acid adducts. Preferred non-ionic surfactants are phenol-ethylene oxide condensates and modified alkyl resins. Examples of suitable anionic surfactants are polyether sulfonates, dialkyl sulfosuccinates, alkyl and alkaryl sulfonates, dialkyl sulfosuccinamides, alkyl sulfates, and phosphate esters. Preferred anionic surfactants are polyether sulfonates and alkyl sulfonates.

Component (C) of the present invention is a freeze-thaw agent. The freeze-thaw agent is glycerine, polyethylene glycol 200, polyethylene glycol 300, propylene glycol, dipropylene glycol, sorbitol, or combination thereof. Glycerine, polyethylene glycol 200, and polyethylene glycol 300 may be used exclusively as the freeze-thaw agent. Propylene glycol, dipropylene glycol, and sorbitol may be used as freeze-thaw agents in combination with glycerine, polyethylene glycol 200, or polyethylene glycol 300. In the case where combinations of freeze-thaw agents are employed, glycerine, polyethylene glycol 200, polyethylene glycol 300, or a combination thereof, must constitute at least 1.7 weight percent of the total combined weight of components (A), (B) and (C).

The freeze-thaw agent is present in an amount of 2.5 to 10 weight percent based on the total combined weight of components (A), (B) and (C). Preferably, the freeze-thaw agent is present in an amount of 4.0 to 6.0 weight percent. The freeze-thaw agent is preferably added after aqueous emulsions (A) and (B) have been combined. The freeze-thaw agent enables the compositions of the present invention to undergo at least one, and usually at least three, freeze-thaw cycle involving temperatures below 0° C. for several hours before thawing without producing a precipitate or solid material in the cosmetic compositions.

The nail coating formulations utilizing the film forming compositions of the present invention can be improved by applying a fixing or crosslinking agent directly to the nails (keratin) before the application of the nail coating formulation. Alternatively, if the fixing agent is formaldehyde, the fixing agent may be incorporated into aqueous emulsion (B) of the nail coating formulation prior to applying the nail coating formulation to the nails. The fixing or crosslinking agents may be dissolved in water, acetone or a mixture of water and acetone at levels of about 1 to about 10 weight percent. Preferred are solutions containing about 1% $ZnCl_2$, 4% water and 95% acetone, percentages by weight, or a solution containing 90 to 95 weight percent acetone and 5 to 10 weight percent of a triamine.

Useful fixing or crosslinking agents include divalent metals, trivalent metals, aldehydes, amino acids, diamines and triamines. Specific examples include zinc chloride, zinc acetate, formaldehyde, alanine and cystine. Preferred amines contain a polymeric portion consisting of poly(oxyalkylene), such as JEFFAMINE 600 and 2000, available from Texaco Chemical Company. Formaldehyde has been found to be especially effective as a fixing agent in the case where a fixing agent is incorporated into a nail coating formulation, which contains the compositions of the present invention, prior to applying the nail coating formulation to the nails.

The combination of aqueous emulsions (A) and (B) and the freeze-thaw agent (C) to be used in nail coating formulations have a total solids content from about 30 to about 65 percent, with a preferred range of from 40 to 52 percent. The total solids content of the aqueous emulsions (A) and (B) is controlled by the relative amounts of polymers which are used in the polymerization reactions and by the amount of water added during the polymerizations. The total solids content can be lower than 30 percent, but too low a solids content increases drying time and is not economical. To obtain the optimum thickness of a coating, the higher solids content is preferred. If the total solids content goes above 65 percent, viscosity increases rapidly and the viscosity will be too high to result in a suitable product.

Many other ingredients can be added to the compositions of the present invention to enhance the performance properties of the nail polish. For example, suspending agents, preservatives, colorants, dispersing agents, wetting agents, thickeners, coalescing agents, antifoams, buffers, chelating agents and ultraviolet light absorbing agents, fillers, and the like, can be included herein. All of these additives and the use thereof are well known in the art. Any of these compounds can be used so long as they do not hinder the present invention from accomplishing its objects.

The freeze-thaw stable cosmetic formulations of the present invention are useful in cosmetics where film forming properties are desired. The compositions of the present invention are especially useful in nail coating formulations. To obtain the most effective utilization of the compositions of this invention as nail coatings, it is recommended that the nails be cleaned prior to applying the nail coating composition. Useful cleaning compounds include low molecular weight alcohols such as ethyl alcohol, ethyl acetate, acetone, toluene, xylene and the like.

The invention will be further illustrated by a consideration of the following examples, which are intended to be exemplary of the invention. All parts and percentages in the examples are on a weight basis unless otherwise stated.

EXAMPLE 1

Sulfopolyester, component (1), was prepared by the following procedure.

A mixture containing 73.66 grams isophthalic acid (0.44375 moles), 15.08 grams of 5-sodiosulfoisophthalic acid (0.05625 moles), 68.1 grams of diethylene glycol (0.6425 moles), 15.48 grams of 1,4-cyclohexanedimethanol (0.1075 moles), 0.19 grams of titanium isopropoxide, and 0,847 grams of sodium acetate tetrahydrate, was prepared. The mixture was placed in a 500 mL round bottom flask under a nitrogen atmosphere. The flask was immersed in a Belmont bath. The mixture was heated with stirring to 200° C. After two hours, the temperature was increased to 280° C. and maintained for one hour under reduced pressure of 0.5 to 0.1 mm of Hg. The flask was allowed to cool to room temperature and the sulfopolyester was removed from the flask. The sulfopolyester had an I.V. of about 0.45 and a glass transition temperature of about 30° C. as measured using a differential scanning calorimeter (DSC). The sulfopolyester which was transparent and amorphous was extruded and pelletized.

EXAMPLE 2

Aqueous Emulsion (A) was prepared by the following procedure.

A mixture containing 856.0 grams of the sulfopolyester prepared in Example 1, 1384.0 grams of deionized water, and 6.0 grams of ammonium persulfate, was prepared. The mixture was heated to 70° C. and 1400 grams of vinyl acetate and 360.0 grams of dibutyl maleate were added over a period of three hours while the mixture underwent agitation. The temperature and agitation were maintained for four additional hours before cooling the mixture to room temperature.

The pH of the aqueous emulsion (A) was adjusted to 5.0–5.5 by the addition of concentrated ammonium hydroxide and the emulsion was filtered through a 53 μm nylon mesh filter. The emulsion had a weight average molecular weight of 58,998 and a number average molecular weight of 8,095 as measured by gel permeation chromatography (GPC). Content of solids was about 50% by weight.

Aqueous emulsion (A) consisted of about 12% by weight of sulfopolyester, 88% by weight of copolymers of vinyl acetate and dibutyl maleate, by weight of total polymer or solids. The vinyl acetate derived units made up about 70% by weight and the dibutyl maleate derived units made up about 18% by weight of the total polymer composition.

EXAMPLE 3

Aqueous Emulsion (B) was prepared by the following procedure.

A mixture containing 1690.0 grams of deionized water and 21.0 grams of Alipal CO-436, an anionic surfactant (Rhone-Poulenc), was prepared. The mixture was placed in a three liter jacketed flask equipped with an agitator, nitrogen sparge and a temperature probe. The mixture was heated to 80° C. under a surface nitrogen sparge. A monomer blend containing 296.1 grams of acetoacetoxyethyl methacrylate, 195.3 grams of butyl acrylate and 768.6 grams of ethyl methacrylate, was prepared. Ammonium persulfate (1.26 grams) was dissolved in 200 grams of water. A portion of the monomer blend, 126 grams, was added to the flask followed by addition of a portion (20 g) of the ammonium persulfate initiator solution and agitation was continued. Following an exotherm, the remaining monomer blend was added under the surface with a simultaneous dropwise addition of the ammonium persulfate initiator solution over a period of three hours. The temperature was maintained at 80° C. throughout the addition of monomers and for an additional twenty minutes while the remainder of the ammonium persulfate initiator solution was added.

After cooling to room temperature, the emulsion which had a solids content of about 40% by weight was filtered through a medium paint filter to remove any large particles. Particle size determination showed an effective particle Size of about 0.1 nm. By GPC analysis, a weight average molecular weight of 251,658 and a number average molecular weight of 83,741 were determined.

EXAMPLES 4–12

Nail coating compositions were prepared by combining Aqueous Emulsion (A) prepared in Example 2 and Aqueous Emulsion (B) prepared in Example 3 and then adding a freeze-thaw agent consisting of glycerine or polyethylene glycol 200 alone or in combination with propylene glycol, dipropylene glycol and/or sorbitol at room temperature with stirring to produce formulations having the weight percentages as listed in Table I.

The nail coating compositions thus prepared were then placed in a freezer at a temperature of −15° C. for 18 hours with no agitation and then allowed to warm to room temperature and checked for instability, i.e. solids being present in the sample. The freeze-thaw cycle was repeated three times or until a considerable level of solids was observed. The test results are summarized in Table I.

The results in Table I clearly show that certain freeze-thaw agents added in a critical amount to cosmetic film forming compositions consisting of an aqueous emulsion comprising a sulfopolyester and a copolymer of vinyl acetate and dialkyl maleate, and an aqueous emulsion comprising the reaction product of acetoacetoxyethyl alkylacrylate with a vinylfunctional monomer, produce freeze-thaw stable cosmetic film forming compositions. Such compositions were exposed to three freeze-thaw cycles involving temperatures below 0° C. for several hours to produce solidification of the composition and then allowed to thaw. No undesirable solid material was found in the samples prepared according to the present invention.

EXAMPLE 13

Comparative Example Without Freeze-Thaw Agent

A nail coating composition was prepared by combining 80 parts by weight of Aqueous Emulsion (A) prepared in Example 2, and 20 parts by weight of Aqueous Emulsion (B) prepared in Example 3, by stirring the components at room temperature. The formulation was subjected to one freeze-thaw cycle as described in Examples 4–11 and the results are listed in Table II. The sample solidified after only one freeze-thaw test.

EXAMPLES 14–40

Comparative Examples

Nail coating compositions were prepared by combining by stirring at room temperature Aqueous Emulsion polymer (A) prepared in Example 2, Aqueous Emulsion polymer (B) prepared in Example 3, with one or more suspected freeze-thaw agent in the amounts as listed in Table II.

The results in Table II as viewed in connection with the results in Table I clearly show that only glycerine, polyethylene glycol 200, polyethylene glycol 300, propylene glycol, dipropylene glycol, and sorbitol will work as freeze-thaw agents in the present invention. Moreover, the data indicates that glycerine, polyethylene glycol 200, and polyethylene glycol 300 may be used exclusively as the freeze-thaw agent, however, propylene glycol, dipropylene glycol, and sorbitol may be used as freeze-thaw agents only if used in combination with glycerine, polyethylene glycol 200, or polyethylene glycol 300. In the case where a combination of such freeze-thaw agents are employed, glycerine, polyethylene glycol 200, or polyethylene glycol 300, must constitute at least 1.7 weight percent of the total combined weight of components (A), (B) and (C).

The data also establishes a critical range for the freeze-thaw agents. The freeze-thaw agent must be present in an amount of 2.5 to 10 weight percent based on the total combined weight of components (A), (B) and (C). It is clear that the preferred range is 4.0 to 6.0 weight percent. Consequently, all of the comparative examples in Table II exhibited poor freeze-thaw stability, with a large amount of solid being observed in each sample after only one cycle.

In addition, some of the examples which contained various levels of isopropanol and ethanol had increased viscosity levels which adversely affected their usefulness as cosmetic film forming compositions.

EXAMPLES 41–48

The nail coating formulation of Examples 4–11 were individually applied to fingernails which had been cleaned with either Solution A, B, C or D.

Solution A was prepared by dissolving 1.0 gram of $ZnCl_2$ in a mixture containing 95.0 grams of acetone and 4.0 grams of deionized water.

Solution B was prepared by dissolving 5.6 grams of JEFFAMINE 600, which is available from Texaco Chemical Company, in 94.4 grams of acetone.

Solution C was prepared by dissolving 2.0 grams of aluminum ammonium sulfate in a mixture containing 60.0 grams of acetone and 38.0 grams of deionized water.

Solution D was HYDROTRITICUM 2000 which is a hydrolyzed whole wheat protein available from Croda, Inc.

In each case the nail polish dried in less than one minute and exhibited a glossy finish, good vapor transmission, adhesion and durability. In addition, no chipping was observed after four days of wear.

EXAMPLE 49

A mixture containing 10.0 grams of Aqueous Emulsion (B) prepared in Example 3 was blended with 1.14 grams of a 37% formaldehyde solution in deionized water. A portion of Aqueous Emulsion (B), 1.9 grams, was blended with 7.6 grams of Aqueous Emulsion (A) of Example 2, 0.5 grams of glycerine and 1.1 grams of finely divided red pigment (D & C Red 17).

The nail polish was applied to fingernails which had been cleaned with acetone. The nail polish dried in less than one minute and exhibited a glossy finish, good vapor transmission, excellent adhesion and durability. In addition, no chipping was observed after four days of wear.

TABLE I

EFFECT OF ADDING FREEZE-THAW AGENTS

| EX. | AQUEOUS EMULSION (A) (wt %) | AQUEOUS EMULSION (B) (wt %) | FREEZE-THAW AGENT (wt %) | FREEZE-THAW AGENT (type) | NUMBER OF FREEZE-THAW CYCLES (RESULTS) |
|---|---|---|---|---|---|
| 4 | 76.0 | 19.0 | 5.0 | Glycerine | 1 (liquid) 2 (liquid) 3 (liquid) |
| 5 | 72.0 | 18.0 | 5.0 5.0 | Glycerine; Dipropylene glycol | 1 (liquid) 2 (liquid) 3 (liquid) |
| 6 | 72.0 | 18.0 | 5.0 5.0 | Glycerine; Propylene glycol | 1 (liquid) 2 (liquid) 3 (liquid) |
| 7 | 76.0 | 19.0 | 2.5 2.5 | Glycerine; Propylene glycol | 1 (liquid) 2 (liquid) 3 (liquid) |
| 8 | 78.0 | 19.5 | 2.5 | Glycerine | 1 (liquid) 2 (66% solid) |
| 9 | 77.3 | 19.3 | 1.7 1.7 | Glycerine; Propylene glycol | 1 (liquid) 2 (90% solid) |
| 10 | 76.0 | 19.0 | 1.67 1.67 1.67 | Glycerine; Propylene glycol; Dipropylene glycol | 1 (liquid) 2 (90% solid) |
| 11 | 76.0 | 19.0 | 2.5 2.5 | Glycerine Sorbitol | 1 (liquid) 2 (liquid) 3 (liquid) |
| 12 | 76.0 | 19.0 | 5.0 | PEG 200 | 1 (liquid) 2 (liquid) 3 (liquid) |

TABLE II

EFFECT OF ADDING FREEZE-THAW AGENTS
(Comparative Examples)

| EX. | AQUEOUS EMULSION (A) (wt %) | AQUEOUS EMULSION (B) (wt %) | FREEZE-THAW AGENT (wt %) | FREEZE-THAW AGENT (type) | NUMBER OF FREEZE-THAW CYCLES (RESULTS) |
|---|---|---|---|---|---|
| 13 | 80.0 | 20.0 | — | — | 1 (solid) |
| 14 | 79.2 | 19.8 | 1.0 | Propylene glycol | 1 (solid) |
| 15 | 78.0 | 19.5 | 2.5 | Propylene glycol | 1 (solid) |
| 16 | 76.0 | 19.0 | 5.0 | Propylene glycol | 1 (solid) |

TABLE II-continued
EFFECT OF ADDING FREEZE-THAW AGENTS
(Comparative Examples)

| EX. | AQUEOUS EMULSION (A) (wt %) | AQUEOUS EMULSION (B) (wt %) | FREEZE-THAW AGENT (wt %) | FREEZE-THAW AGENT (type) | NUMBER OF FREEZE-THAW CYCLES (RESULTS) |
|---|---|---|---|---|---|
| 17 | 72.0 | 19.0 | 10.0 | Propylene glycol | 1 (solid) |
| 18 | 78.0 | 19.5 | 2.5 | Dipropylene glycol | 1 (solid) |
| 19 | 76.0 | 19.0 | 5.0 | Dipropylene glycol | 1 (90% solid) |
| 20 | 78.0 | 19.5 | 2.5 | Monoacetin | 1 (solid) |
| 21 | 76.0 | 19.0 | 5.0 | Monoacetin | 1 (90% solid) |
| 22 | 76.0 | 19.0 | 5.0 | Sorbitol | 1 (solid) |
| 23 | 72.0 | 18.0 | 5.0 5.0 | Propylene glycol; Dipropylene glycol | 1 (50% solid) |
| 24 | 72.0 | 18.0 | 10.0 | Dipropylene glycol | 1 (50% solid) |
| 25 | 76.0 | 19.0 | 5.0 | Squalane | 1 (solid) |
| 26 | 76.0 | 19.0 | 5.0 | Mineral oil | 1 (solid) |
| 27 | 76.0 | 19.0 | 5.0 | Triacetin | 1 (solid) |
| 28 | 76.0 | 19.0 | 5.0 | Isopropanol | 1 (solid) |
| 29 | 72.0 | 18.0 | 10.0 | Isopropanol | 1 (solid) |
| 30 | 64.0 | 16.0 | 20.0 | Isopropanol | 1 (50% solid) |
| 31 | 76.0 | 19.0 | 5.0 | Ethanol | 1 (75% solid) |
| 32 | 72.0 | 18.0 | 10.0 | Ethanol | 1 (25% solid) |
| 33 | 64.0 | 16.0 | 20.0 | Ethanol | 1 (10% solid) |
| 34 | 78.0 | 19.5 | 0.83 0.83 0.83 | Glycerine; Propylene glycol; Dipropylene glycol | 1 (50% solid) |
| 35 | 77.3 | 19.3 | 1.7 1.7 | Propylene glycol; Dipropylene glycol | 1 (50% solid) |
| 36 | 76.0 | 19.0 | 2.5 2.5 | Propylene glycol; Dipropylene glycol | 1 (33% solid) |
| 37 | 76.0 | 19.0 | 2.5 2.5 | Glycerine; Ethyl Alcohol | 1 (soft solid) |
| 38 | 76.0 | 19.0 | 2.5 2.5 | Glycerine; Monoacetin | 1 (soft solid) |
| 39 | 76.0 | 19.0 | 2.5 2.5 | Glycerine; n-Propyl alcohol | 1 (soft solid) |
| 40 | 76.0 | 19.0 | 5.0 | n-Propyl alcohol | 1 (soft solid) |

Many variations will suggest themselves to those skilled in this art in light of the above detailed description. All such obvious modifications are within the full intended scope of the appended claims.

What is claimed is:

1. A freeze-thaw stable cosmetic film forming composition capable of withstanding at least one freeze-thaw cycle involving temperatures below 0° C. for up to eighteen hours before thawing without producing a precipitate, said composition comprising:

(A) 27.5 to 85 weight percent of an aqueous emulsion comprising
  (1) a sulfopolyester consisting essentially of repeat units from
    (a) a dicarboxylic acid selected from the group consisting of aromatic dicarboxylic acids, saturated aliphatic dicarboxylic acids, cycloaliphatic dicarboxylic acids, and combinations thereof;
    (b) a diol; and
    (c) a difunctional sulfomonomer containing at least one sulfonate group attached to an aromatic nucleus wherein the functional groups are hydroxy, carboxy or amino, provided the difunctional sulfomonomer is present in an amount from 4 to 25 mole percent based on 100 mole percent dicarboxylic acid and 100 mole percent diol; and
  (2) a copolymer having repeat units from 50 to 90 weight percent vinyl acetate and 10 to 50 weight percent of a dialkyl maleate or fumarate having the formula

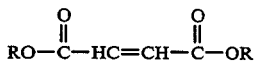

which is polymerized in an aqueous dispersion of the sulfopolyester;

(B) 12.5 to 70 weight percent of an aqueous emulsion of an addition polymer derived by emulsion polymerization of acetoacetoxyethyl alkylacrylate having the formula:

or a polymerization reaction product of acetoacetoxyethyl alkylacrylate with a vinyl-functional monomer selected from the group consisting of

 (I)

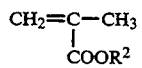 (II)

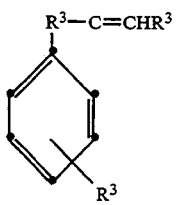

and mixtures thereof;
wherein: R is a monovalent alkyl radical having 1 to 12 carbon atoms, $R^1$ is a monovalent alkyl radical having 1 to 4 carbon atoms, $R^2$ is selected from the group consisting of an alkyl radical having 1 to 20 carbon atoms, a substituted alkyl radical having 1 to 20 carbon atoms, phenyl, substituted phenyl, cycloalkyl, furfuryl, and tetrahydrofurfural, and $R^3$ is independently selected from the group consisting of hydrogen and an alkyl radical having 1 to 4 carbon atoms; and (C) 2.5 to 10 weight percent of a freeze-thaw agent selected from the group consisting of glycerine, polyethylene glycol 200, polyethylene glycol 300, and combination thereof; provided that the total solids in the film forming composition is from 30 to 65 weight percent.

2. A freeze-thaw stable cosmetic film forming composition capable of withstanding at least one freeze-thaw cycle involving temperatures below 0° C. for up to eighteen hours before thawing without producing a precipitate, said composition comprising:

(A) 27.5 to 85 weight percent of an aqueous emulsion comprising
   (1) a sulfopolyester consisting essentially of repeat units from
      (a) a dicarboxylic acid selected from the group consisting of aromatic dicarboxylic acids, saturated aliphatic dicarboxylic acids, cycloaliphatic dicarboxylic acids, and combinations thereof;
      (b) a diol; and
      (c) a difunctional sulfomonomer containing at least one sulfonate group attached to an aromatic nucleus wherein the functional groups are hydroxy, carboxy or amino, provided the difunctional sulfomonomer is present in an amount from 4 to 25 mole percent based on 100 mole percent dicarboxylic acid and 100 mole percent diol; and
   (2) a copolymer having repeat units from 50 to 90 weight percent vinyl acetate and 10 to 50 weight percent of a dialkyl maleate or fumarate having the formula

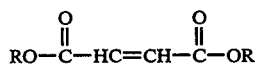

which is polymerized in an aqueous dispersion of the sulfopolyester;

(B) 12.5 to 70 weight percent of an aqueous emulsion of an addition polymer derived by emulsion polymerization of acetoacetoxyethyl alkylacrylate having the formula:

or a polymerization reaction product of acetoacetoxyethyl alkylacrylate with a vinyl-functional monomer selected from the group consisting of

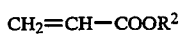 (I)

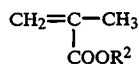 (II)

-continued

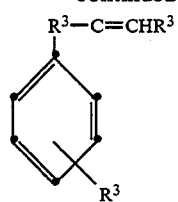

and mixtures thereof;
wherein: R is a monovalent alkyl radical having 1 to 12 carbon atoms, $R^1$ is a monovalent alkyl radical having 1 to 4 carbon atoms, $R^2$ is selected from the group consisting of an alkyl radical having 1 to 20 carbon atoms, a substituted alkyl radical having 1 to 20 carbon atoms, phenyl, substituted phenyl, cycloalkyl, furfuryl, and tetrahydrofurfural, and $R^3$ is independently selected from the group consisting of hydrogen and an alkyl radical having 1 to 4 carbon atoms;

(C) 2.5 to 10 weight percent of a freeze-thaw agent selected from the group consisting of glycerine, polyethylene glycol 200, polyethylene glycol 300, and combination thereof; and (D) a fixing agent; provided that the total solids in the film forming composition is from 30 to 65 weight percent.

3. A freeze-thaw stable cosmetic film forming composition capable of withstanding at least one freeze-thaw cycle involving temperatures below 0° C. for up to eighteen hours before thawing without producing a precipitate, said composition comprising:

(A) 27.5 to 85 weight percent of an aqueous emulsion comprising
   (1) a sulfopolyester consisting essentially of repeat units from
      (a) a dicarboxylic acid selected from the group consisting of aromatic dicarboxylic acids, saturated aliphatic dicarboxylic acids, cycloaliphatic dicarboxylic acids, and combinations thereof;
      (b) a diol; and
      (c) a difunctional sulfomonomer containing at least one sulfonate group attached to an aromatic nucleus wherein the functional groups are hydroxy, carboxy or amino, provided the difunctional sulfomonomer is present in an amount from 4 to 25 mole percent based on 100 mole percent dicarboxylic acid and 100 mole percent diol; and
   (2) a copolymer having repeat units from 50 to 90 weight percent vinyl acetate and 10 to 50 weight percent of a dialkyl maleate or fumarate having the formula

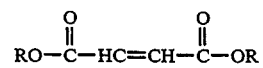

which is polymerized in an aqueous dispersion of the sulfopolyester;

(B) 12.5 to 70 weight percent of an aqueous emulsion of an addition polymer derived by emulsion polymerization of acetoacetoxyethyl alkylacrylate having the formula:

or a polymerization reaction product of acetoacetoxyethyl alkylacrylate with a vinyl-functional monomer selected from the group consisting of

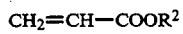 (I)

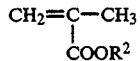 (II)

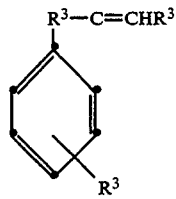

and mixtures thereof;
wherein: R is a monovalent alkyl radical having 1 to 12 carbon atoms, $R^1$ is a monovalent alkyl radical having 1 to 4 carbon atoms, $R^2$ is selected from the group consisting of an alkyl radical having 1 to 20 carbon atoms, a substituted alkyl radical having 1 to 20 carbon atoms, phenyl, substituted phenyl, cycloalkyl, furfuryl, and tetrahydrofurfural, and $R^3$ is independently selected from the group consisting of hydrogen and an alkyl radical having 1 to 4 carbon atoms; and (C) 2.5 to 10 weight percent of a freeze-thaw agent which is added after aqueous emulsions (A) and (B) have been combined, said freeze-thaw agent being selected from the group consisting of glycerine, polyethylene glycol 200, polyethylene glycol 300, and combination thereof; provided that the total solids in the film forming composition is from 30 to 65 weight percent.

4. The cosmetic film forming composition of claim 1 wherein the total solids in the composition is 45 to 52 percent.

5. The cosmetic film forming composition of claim 1 wherein the freeze-thaw agent is selected from the group consisting of glycerine, polyethylene glycol 200, polyethylene glycol 300, and combination thereof.

6. The cosmetic film forming composition of claim 1 wherein the freeze-thaw agent is a combination of glycerine and propylene glycol.

7. The cosmetic film forming composition of claim 1 wherein the freeze-thaw agent is a combination of glycerine and dipropylene glycol.

8. The cosmetic film forming composition of claim 1 wherein the freeze-thaw agent is a combination of glycerine and sorbitol.

9. The cosmetic film forming composition of claim 1 wherein the freeze-thaw agent is present in an amount of 4.0 to 6.0 weight percent.

10. The aqueous emulsion (A) of claim 1 wherein the dicarboxylic acid component is selected from the group consisting of terephthalic acid, phthalic acid, isophthalic acid, naphthalene-2,6-dicarboxylic acid, cyclohexanedicarboxylic acid, cyclohexanediacetic acid, and mixtures thereof.

11. The aqueous emulsion (A) of claim 10 wherein the dicarboxylic acid component is isophthalic acid.

12. The aqueous emulsion (A) of claim 1 wherein the diol component is selected from the group consisting of ethylene glycol, diethylene glycol, triethylene glycol, 1,4-cyclohexanedimethanol, and mixtures thereof.

13. The aqueous emulsion (A) of claim 12 wherein the diol component is diethylene glycol and 1,4-cyclohexanedimethanol.

14. The aqueous emulsion (A) of claim 1 wherein the difunctional sulfomonomer component is 5-sodiosulfoisophthalic acid.

15. The aqueous emulsion (A) of claim 1 wherein the sulfopolyester component has repeat units from isophthalic acid, diethylene glycol and 1,4-cyclohexanedimethanol, and 5-sodiosulfoisophthalic acid.

16. The aqueous emulsion (A) of claim 1 wherein the sulfopolyester component and copolymer component are present in an amount of from 5 to 20 and 95 to 80 weight percent respectively.

17. The aqueous emulsion (B) of claim 1 wherein the acetoacetoxyethyl alkylacrylate is acetoacetoxyethyl methacrylate.

18. The aqueous emulsion (B) of claim 1 wherein the vinylfunctional monomer is selected from the group consisting of acrylate esters, methacrylate esters, aromatic vinylfunctional monomers and mixtures thereof.

19. The aqueous emulsion (B) of claim 18 wherein the vinylfunctional monomer is an acrylate ester selected from the group consisting of methyl acrylate, ethyl acrylate, butyl acrylate, benzyl acrylate, furfuryl acrylate, tetrahydrofurfuryl acrylate, methoxyethyl acrylate, ethoxyethyl acrylate, 2-ethylhexyl acrylate, cyclopentyl acrylate, cyclohexyl acrylate, 2,3-epoxy-1-propyl acrylate, 2-dimethylaminoethyl acrylate, lauryl acrylate, and mixtures thereof.

20. The aqueous emulsion (B) of claim 18 wherein the vinylfunctional monomer is a methacrylate ester selected from the group consisting of methyl methacrylate, ethyl methacrylate, propyl methacrylate, butyl methacrylate, phenyl methacrylate, benzyl methacrylate, propyleneglycol monomethacrylate, stearyl methacrylate, tetrahydrofurfuryl methacrylate, furfuryl methacrylate, 2-diethylaminoethyl methacrylate, hydroxyethyl methacrylate, and mixtures thereof.

21. The aqueous emulsion (B) of claim 18 wherein the vinylfunctional monomer is an aromatic vinylfunctional monomer selected from the group consisting of styrene, 4-vinyltoluene, 2-vinyltoluene, a-methylstyrene, 4-isopropylstyrene, diisopropenyl benzene, and mixtures thereof.

22. The aqueous emulsion (B) of claim 18 wherein the vinylfunctional monomer is selected from the group consisting of butyl acrylate, methyl methacrylate, ethyl acrylate and mixtures thereof.

23. The aqueous emulsion (B) of claim 1 wherein an additional vinylfunctional monomer is employed along with the vinylfunctional monomer of Formulas I, II, or III, in an amount not exceeding 10 weight percent of the total amount of vinylfunctional monomers.

24. The cosmetic film forming composition of claim 2 wherein the fixing agent, Component (C), is selected from the group consisting of divalent metals, trivalent metals, aldehydes, amino acids, diamines, triamines, and mixtures thereof.

25. The cosmetic film forming composition of claim 2 wherein the fixing agent, component (C), is selected from the group consisting of zinc chloride, zinc acetate, formaldehyde, alanine and cystine.

26. A method for preparing a freeze-thaw stable cosmetic film forming composition comprising:
(I) preparing a sulfopolyester consisting essentially of repeat units from
  (a) a dicarboxylic acid selected from the group consisting of aromatic dicarboxylic acids, saturated aliphatic dicarboxylic acids, cycloaliphatic dicarboxylic acids, and combinations thereof;
  (b) a diol; and
  (c) a difunctional sulfomonomer containing at least one sulfonate group attached to an aromatic nucleus wherein the functional groups are hydroxy, carboxy or amino, provided the difunctional sulfomonomer is present in an amount from 4 to 25 mole percent based on 100 mole percent dicarboxylic acid and 100 mole percent diol;
(II) forming an aqueous emulsion (A) which contains the sulfopolyester of (I), and polymerizing vinyl acetate and a dialkyl maleate having the formula

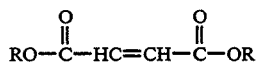

in said aqueous emulsion; and independently
(III) preparing an aqueous emulsion (B) of acetoacetoxyethyl alkylacrylate having the formula:

or a reaction product of acetoacetoxyethyl alkylacrylate with a vinylfunctional monomer selected from the group consisting of $$CH_2=CH-COOR^2 \quad (I)$$

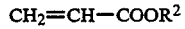

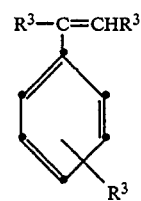

and mixtures thereof 1 wherein: R is a monovalent alkyl radical having 1 to 12 carbon atoms, $R^1$ is a monovalent alkyl radical having 1 to 4 carbon atoms, $R^2$ is selected from the group consisting of an alkyl radical having 1 to 20 carbon atoms, a substituted alkyl radical having 1 to 20 carbon atoms, phenyl, substituted phenyl, cycloalkyl, furfuryl, and tetrahydrofurfural, and $R^3$ is independently selected from the group consisting of hydrogen and an alkyl radical having 1 to 4 carbon atoms;

(IV) mixing aqueous emulsions (A) and (B) to thereby obtain an aqueous dispersion of a blend of polymers; and (V) adding 2.5 to 10 weight percent, based on the total combined weight of components (A), (B), and (C), of a freeze-thaw agent to the mixture, said freeze-thaw agent being selected from the group consisting of glycerine, polyethylene glycol 200, polyethylene glycol 300, propylene glycol, dipropylene glycol, sorbitol, and combination thereof; provided that glycerine, polyethylene glycol 200, polyethylene glycol 300 or combinations thereof constitute at least 1.7 weight percent of the total combined weight of components (A), (B) and (C); and further provided that the total solids in the film forming composition is from 30 to 65 weight percent.

* * * * *